United States Patent
Hartley et al.

(10) Patent No.: US 7,645,298 B2
(45) Date of Patent: Jan. 12, 2010

(54) STENT GRAFT FENESTRATION

(75) Inventors: David Ernest Hartley, Subiaco (AU); Frank Karhu Christiansen, Haslev (DK)

(73) Assignees: William A. Cook Australia Pty. Ltd., Queensland (AU); Cook Incorporated, Bloomington, IN (US)

( * ) Notice: Subject to any disclaimer, the term of this patent is extended or adjusted under 35 U.S.C. 154(b) by 237 days.

(21) Appl. No.: 10/962,646

(22) Filed: Oct. 12, 2004

(65) Prior Publication Data

US 2005/0131517 A1 Jun. 16, 2005

Related U.S. Application Data

(60) Provisional application No. 60/549,307, filed on Mar. 2, 2004, provisional application No. 60/510,593, filed on Oct. 10, 2003.

(51) Int. Cl.
*A61F 2/06* (2006.01)
(52) U.S. Cl. ............... 623/1.35; 623/1.13; 623/1.15
(58) Field of Classification Search ............ 623/1.32, 623/1.35, 1.13, 1.15, 1.16, 1.3; 606/157, 606/151, 153
See application file for complete search history.

(56) References Cited

U.S. PATENT DOCUMENTS

| | | | | |
|---|---|---|---|---|
| 5,609,627 | A * | 3/1997 | Goicoechea et al. | 128/898 |
| 5,984,955 | A * | 11/1999 | Wisselink | 623/1.35 |
| 6,471,722 | B1 * | 10/2002 | Inoue | 623/1.35 |
| 2004/0193254 | A1 * | 9/2004 | Greenberg et al. | 623/1.35 |
| 2006/0095118 | A1 * | 5/2006 | Hartley | 623/1.35 |
| 2006/0136046 | A1 * | 6/2006 | Hartley et al. | 623/1.35 |
| 2006/0287712 | A1 * | 12/2006 | Eidenschink | 623/1.35 |
| 2007/0244542 | A1 * | 10/2007 | Greenan et al. | 623/1.13 |

FOREIGN PATENT DOCUMENTS

WO    WO 97/27898    * 8/1997

* cited by examiner

*Primary Examiner*—Anhtuan T Nguyen
*Assistant Examiner*—Sarah A Simpson
(74) *Attorney, Agent, or Firm*—Richard J. Godlewski

(57) ABSTRACT

A stent graft (20) has a tubular body of graft material (21), a number of self expanding stents (67) associated with the tubular body to define a fluid flow path through the stent graft when the self expanding stents are in their expanded configurations. At least one fenestration (22) in the tubular body is adapted to receive a side arm stent graft (71) to provide a fluid flow path from the tubular body and through the side arm stent graft. The or each fenestration has at least an inner ring (26) and an outer ring (24) and graft material (28) extending from the inner ring to the outer ring and the outer ring being in the tubular body of graft material. The inner ring can be hinged (31) to the outer ring or concentric within the outer ring. An intermediate ring (86) may also be used between the inner and outer rings.

7 Claims, 4 Drawing Sheets

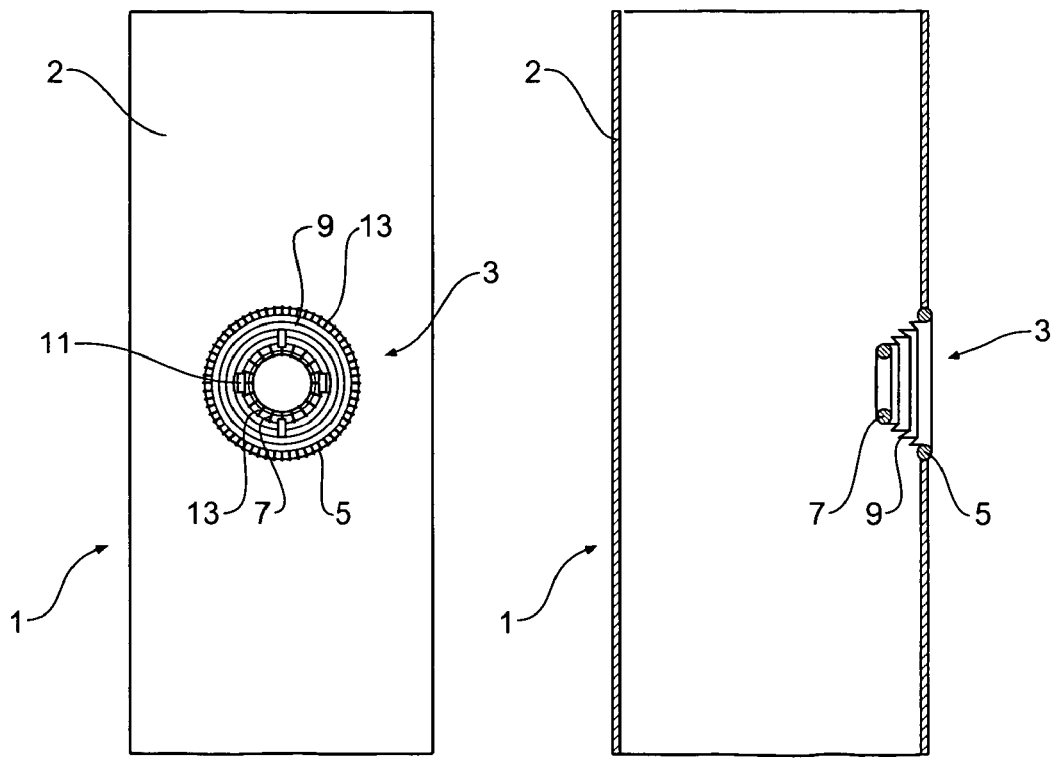
*Fig 1*  *Fig 2*
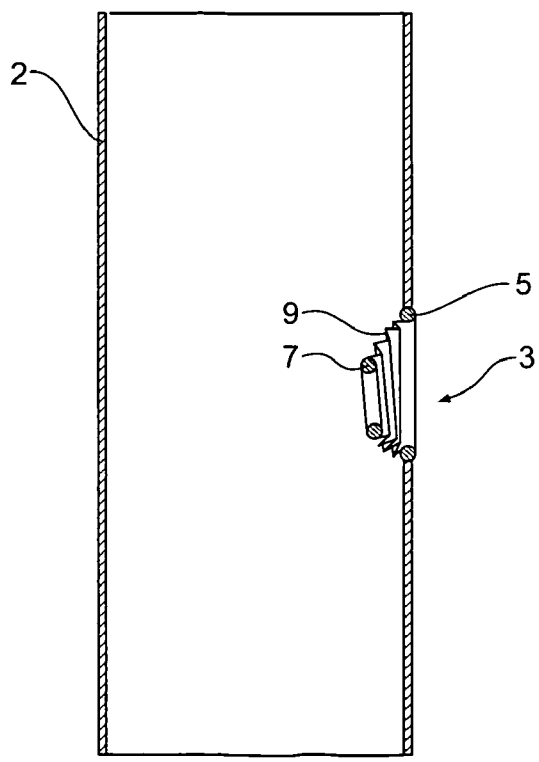
*Fig 3*

STENT GRAFT FENESTRATION

CROSS-REFERENCE TO RELATED APPLICATIONS

This application claims priority of provisional application Ser. No. 60/510,593, filed Oct. 10, 2003 and Ser. No. 60/549,307, filed Mar. 2, 2004.

TECHNICAL FIELD

This invention relates to a stent graft and more particularly to the positioning and construction of a fenestration in a stent graft.

BACKGROUND OF THE INVENTION

Stent grafts are used for treatment of vasculature in the human or animal body to bypass a repair or defect in the vasculature. For instance, a stent graft may be used to span an abdominal aortic aneurism. In many cases, however, such damaged or defected portion of the vasculature may include a branch vessel such as a mesenteric artery or a renal artery. Bypassing such an artery without providing blood flow into the branch artery can cause problems and hence it has been proposed to provide a fenestration in the wall of a stent graft which, when the stent graft is deployed, is positioned over the opening to the branch vessel. Another stent graft can be deployed through the fenestration into the branch vessel to provide a blood flow path to the branch artery.

A problem exists, however, in mapping the vasculature so that a fenestration is positioned correctly in relation to the branch vessel when a stent graft is constructed. Where the position of a fenestration with respect to a branch vessel is offset when the stent graft is deployed, it may be difficult to deploy guide wires and catheters from the stent graft into the branch vessel to enable correct positioning of the branch vessel stent graft. Also when the fenestration is offset from the branch and a stent graft is deployed into the branch vessel from a main stent graft, the branch vessel stent graft may be kinked to such an extent that blood flow will not occur through it.

SUMMARY OF THE INVENTION

It is the object of this invention therefore to provide an answer to this problem by providing a stent graft arrangement in which the positioning of the fenestration can be more flexible or variable.

In one form, therefore, the invention is said to reside in a stent graft including a wall and at least one fenestration assembly, the fenestration assembly including a first ring defining a first aperture in the wall of the stent graft and a second ring defining a small aperture within the first ring and graft material extending between the first ring and the second ring, whereby movement of the second ring with respect to the first ring is enabled.

The graft material extending between the first and second rings provides an arrangement which enables movement of the second ring with respect to the first ring such as by orbital or eccentric movement of the second ring with respect to the first ring or by an angular movement of the second ring with respect to the first ring.

Preferably the first ring and the second ring are formed from wire such as nitinol wire, stainless steel wire or any other biocompatible elastic material. There may be two or three turns of wire for each ring. The wire from which the rings may be formed may have a diameter or thickness of from approximately 35 microns to approximately 500 microns.

In one embodiment the first ring and the second ring may be joined by a hinge arrangement. The hinge arrangement may be an integral wire hinge. That is the hinge arrangement may be formed by a portion of the wire or other material from which the rings are made.

In a further embodiment there may be a third ring intermediate the first and second rings. The third ring may be joined to the other rings by an integral hinge and be formed from nitinol wire or the like. In one embodiment the first and second rings may be substantially at right angles to each other and the third ring is between them at an angle of about 45° to each of them. The third ring can provide extra support to a graft material tube fastened to it.

The graft material extending between the first ring and the second ring can be concentrically corrugated whereby to allow flexible positioning of the second ring within the first ring.

Alternatively the graft material extending between the first ring and the second ring can be formed from a biocompatible elastic material whereby to allow flexible positioning of the second ring within the first ring.

The graft material extending between the first ring and the second ring may alternatively be of a substantially frusto-conical shape and extend into or away from the stent graft.

There may be further included radiopaque markers around or concentric with each fenestration. The radiopaque markers may be formed from a biocompatible heavy metal such as gold.

In one arrangement the first ring and the second ring can be substantially concentric or alternatively the second ring can be off-center within the first ring.

Hence the second ring can be joined to the first ring by an integral hinge and the graft material extending between the first ring and the second ring provides a skewed frusto-conical extension into or away from the stent graft whereby the smaller aperture is directed towards a selected end of the stent graft.

In an alternative form, the invention is said to reside in a stent graft comprising a tubular body of graft material, a plurality of self expanding stents associated with the tubular body to define in use a fluid flow path through the stent graft when the self expanding stents are in their expanded configurations, at least one fenestration in the tubular body, each fenestration having an inner ring and an outer ring and graft material extending from the inner ring to the outer ring and the outer ring being received in the tubular body of graft material, each fenestration adapted to receive a side arm stent graft therein whereby to provide a fluid flow path from the tubular body and through the side arm stent graft.

In an alternative form, the invention is said to reside in a stent graft comprising a tubular body of graft material, a plurality of self expanding stents associated with the tubular body to define in use a fluid flow path through the stent graft when the self expanding stents are in their expanded configurations, at least one fenestration assembly mounted about an aperture in the tubular body, each fenestration having an inner ring, an outer ring and an intermediate ring and graft material extending from the inner ring to the outer ring and fastened to the intermediate ring and the outer ring being mounted into the tubular body of graft material, each fenestration adapted to receive a side arm stent graft therein whereby to provide a fluid flow path from the tubular body and through the side arm stent graft.

The fenestration may include a graft material tube extending from the inner ring and at least one self expanding stent on the graft material tube extending beyond the inner ring.

The fenestration assembly may be mounted into an aperture in the wall of a stent graft so that the fenestration assembly extends inside or outside of the stent graft. Further the fenestration assembly may extend distally or proximally from the fenestration depending upon whether the physician using the device wishes to deploy a guide wire and subsequently a side arm stent graft into the fenestration assembly from a distal or proximal end of the vessel into which the stent graft is deployed.

The graft material may be a synthetic material such as Dacron, THORALON™, expanded polytetrafluoroethylene (ePTFE), or other synthetic biocompatible material. Alternatively a naturally occurring biomaterial, such as collagen, is highly desirable, particularly a specially derived collagen material known as an extracellular collagen matrix (ECM) material, such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data show that the SIS used in venous valves can be replaced by native tissue in as little as a month's time. In addition to xenogenic biomaterials, such as SIS, autologous tissue can be harvested as well. Additionally Elastin or Elastin-Like Polypeptides (ELPs) and the like offer potential as a material to fabricate the covering or frame to form a device with exceptional biocompatibility. Another alternative would be to use allographs such as harvested native valve tissue. Such tissue is commercially available in a cryopreserved state.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

U.S. Pat. No. 6,524,335 and PCT Patent Publication No. WO 99/29262 entitled "Endoluminal Aortic Stents" disclose a fenestrated prosthesis for placement where there are intersecting arteries. This feature and other features disclosed in U.S. Pat. No. 6,524,335 and PCT Patent Publication No. WO 99/29262 could be used with the present invention and the disclosure of U.S. Pat. No. 6,524,335 and PCT Patent Publication No. WO 99/29262 is herewith incorporated in its entirety into this specification.

U.S. patent application Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. patent application Ser. No. 10/280,486, and U.S. Patent Application Publication No. US-2003-0088305-A1 and PCT Patent Publication No. WO 03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003, and Published on Dec. 18, 2003, as U.S. Patent Application Publication No. US-2003-0233140-A1 entitled "Trigger Wires" disclose release wire systems for the release of stent grafts retained on introducer devices. This feature and other features disclosed in U.S. Provisional Patent Application Ser. No. 60/392,682 and U.S. patent application Ser. No. 10/447,406, filed May 29, 2003 could be used with the present invention and the disclosure of U.S. Provisional Patent Application Ser. No. 60/392,682 and U.S. patent application Ser. No. 10/447,406, filed May 29, 2003 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003, and Published on May 20, 2004, as U.S. Patent Application Publication No. US-2004-0098079-A1, and PCT Patent Publication No. WO 2004/028399 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and U.S. Patent Application Publication No. US-2004-0098079-A1, and PCT Patent Publication No. WO 2004/028399 could be used with the present invention and the disclosure of U.S. Provisional Patent Application Ser. No. 60/392,667, U.S. patent application Ser. No. 10/609,846, and U.S. Patent Application Publication No. US-2004-0098079-A1, and PCT Patent Publication No. WO 2004/028399 is herewith incorporated in its entirety into this specification.

U.S. Provisional Patent Application Ser. No. 60/392,599, filed Jun. 28, 2002, and U.S. patent application Ser. No.

10/609,835, filed Jun. 30, 2003, and published on Jun. 3, 2004, as U.S. Patent Application Publication No. US-2004-0106978-A1, and PCT Patent Publication No. WO 2004/002370 entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 could be used with the present invention, and the disclosure of U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 is herewith incorporated in its entirety into this specification.

U.S. Provisional Patent Application Ser. No. 60/391,737, filed Jun. 26, 2002, U.S. patent application Ser. No. 10/602,930, filed Jun. 24, 2003, and PCT Patent Publication No. WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and PCT Patent Publication Number WO 2004/002365 could be used with the present invention and the disclosure of U.S. Provisional Patent Application Ser. No. 60/391,73, U.S. patent application Ser. No. 10/602,930, and PCT Patent Publication No. WO 2004/002365 are herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and published on Apr. 15, 2004, as U.S. Patent Application Publication No. US-2004-0073289-A1, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 is herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and published on Apr. 29, 2004, as U.S. Patent Application Publication No. US-2004-0082990-A1, and PCT Patent Publication No. WO 2004/017867 entitled "Composite Prostheses" discloses prostheses or stent grafts suitable for endoluminal deployment. These prostheses and other features disclosed in U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 could be used with the present invention and the disclosure of U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 is herewith incorporated in its entirety into this specification.

BRIEF DESCRIPTION OF THE DRAWING

This then generally describes the invention but to assist with understanding, reference will now be made to the accompanying drawings which show preferred embodiments of the invention.

In the drawings:

FIG. 1 shows a side view of a stent graft including a first embodiment of fenestration assembly according to the present invention;

FIG. 2 shows a cross-section view of a stent graft including the fenestration assembly shown in FIG. 1;

FIG. 3 shows the embodiment shown in FIG. 2 with the fenestration offset within the fenestration assembly;

DETAILED DESCRIPTION

Figure 4:
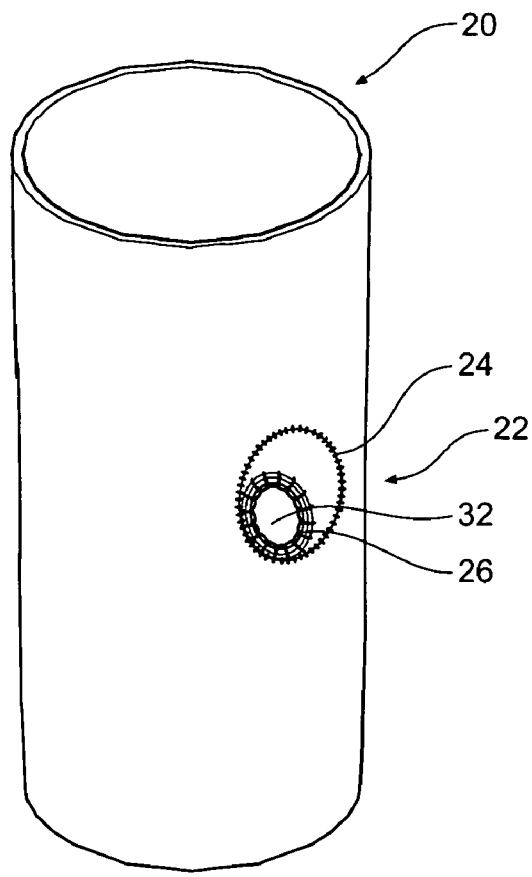
FIG. 4 shows a second embodiment of fenestration assembly in a stent graft according to the present invention.

Now looking at the drawings in more detail and particularly the first embodiment of the invention shown in FIGS. 1 to 3.

In FIGS. 1 to 3 there is shown a stent graft 1 which is a substantially tubular body or wall 2 of graft material and may include self expanding or balloon expandable stents in a well known manner but these are not shown in these illustrations. The tubular body 2 provides a flow path through it for blood or other bodily fluids. To enable a flow path to be established to a branch vessel from a vessel into which the stent graft 1 is deployed, there is provided a fenestration assembly generally shown as 3. The fenestration assembly 3 includes an outer ring 5 in the tubular wall 2 and an inner ring 7 joined by a portion of a biocompatible graft material 9 to the outer ring 5. In this embodiment the portion of graft material 9 is in a conic form with circular or concentric corrugations or can be formed from some other biocompatible flexible material so that, as shown in FIG. 3 for instance, the inner ring 7 can be displaced transversely within the outer ring 5 so that the inner ring 7 can essentially take up a range of positions within the outer ring 7 so that misalignment between the stent graft and the branch vessel may be allowed for both longitudinally or transversely. There may be provided radiopaque markers 11 around the inner ring 7 and if desired also around the outer ring 5 to enable visualisation of the ring with respect to the branch vessel by suitable radiographic techniques when the stent graft is deployed within a human or animal body.

The outer and inner rings 5 and 7 may be manufactured from one, two or three turns of a resilient wire or similar material with the graft material 9 sewn to them with stitching 13. The resilient wire from which the rings 5 and 7 are formed enables the stent graft to be compressed into a contracted condition on a deployment device for deployment using a deployment device.

Figure 5:
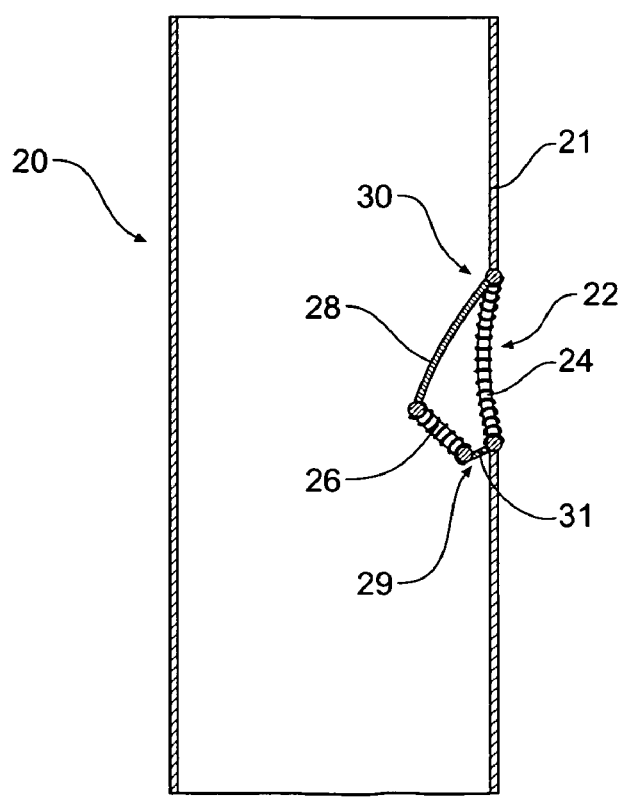
FIG. 5 shows a cross-sectional view of the embodiment shown in FIG. 4.

FIGS. 4 and 5 show an alternative embodiment of stent graft according to the invention.

In this embodiment, the stent graft again comprises a tubular body 20 and may include self expanding or balloon expandable stents in a well known manner but these are not shown in these illustrations. A fenestration assembly 22 is in a wall 21 of the tubular body 20. The fenestration assembly 22 comprises an outer ring 24 and an inner ring 26. Joining the inner and outer rings is a substantially funnel or frusto-conical shaped portion of graft material 28 which is skewed so that the inner ring 26 is much closer to the outer ring 26 at the lower end 29 of the fenestration assembly than the upper end 30. The short piece of material 31 at the end 29 in effect provides a hinge arrangement between the outer ring 24 and the inner ring 26. The inner ring 26 provides an aperture or fenestration 32 through which a side branch stent graft may be deployed.

The inner ring 26 can move angularly with respect to the outer ring 24 so as to allow for misalignment of the fenestration with the branch vessel when the stent graft 20 is positioned within a body lumen.

It will be noted, too, that the open aperture in the smaller ring is directed towards one end of the stent graft. This can be varied to face towards one end or the other of the stent graft depending upon what direction the physician is intending to approach the fenestration. For instance in deployment into the aorta a physician may use either a brachial or a femoral approach.

Figure 6:
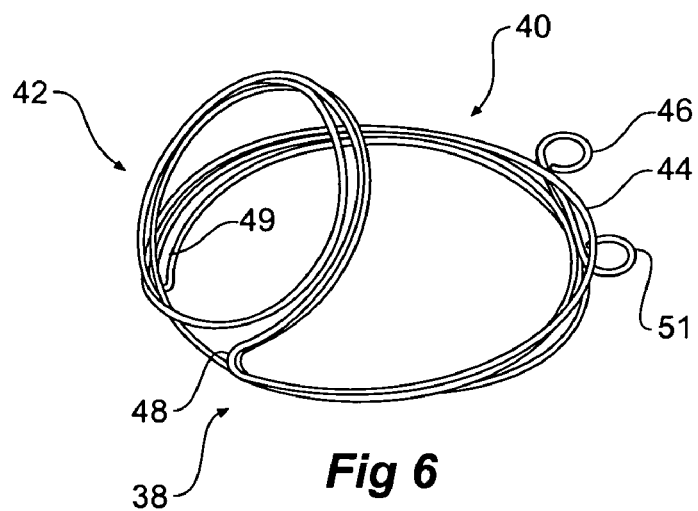
FIG. 6 shows a wire ring arrangement to provide a fenestration according to one embodiment of the invention.

FIG. 6 shows one embodiment by which a ring system may be used to provide an integral hinge arrangement between an outer ring and an inner ring.

In FIG. 6 a ring system 38 comprises an outer ring generally shown as 40 formed from several turns of resilient wire such as nitinol or stainless steel wire and an inner ring generally shown as 42 formed from a number of turns of resilient wire such as nitinol or stainless steel wire. Preferably there is a single piece of wire which forms both the inner and outer rings together connected by a portion or portions of wire to provide an integral hinge arrangement between the inner ring 42 and outer ring 40.

In the embodiment shown, the wire 44 commences at a termination loop 46 and has one and a half turns of the outer ring 40 and then extends to the inner ring 42 and does one complete turn of that ring before recommencing a further turn of the outer ring. Just before the completion of one full turn of the outer ring there is a sharp bend 48 and the wire does most of a turn of the inner ring 42 before another sharp bend 49 in which the wire recommences a turn of the outer ring 40 until it gets to the final termination loop 51. Each of the termination loops 46 and 51 are provided so that there is not any "sharp" end of the wire which may tend to puncture the graft material or the vasculature. The use of nitinol or other resilient wire enables the device to be compressed when it is constrained for deployment in a deployment device.

Figure 7:
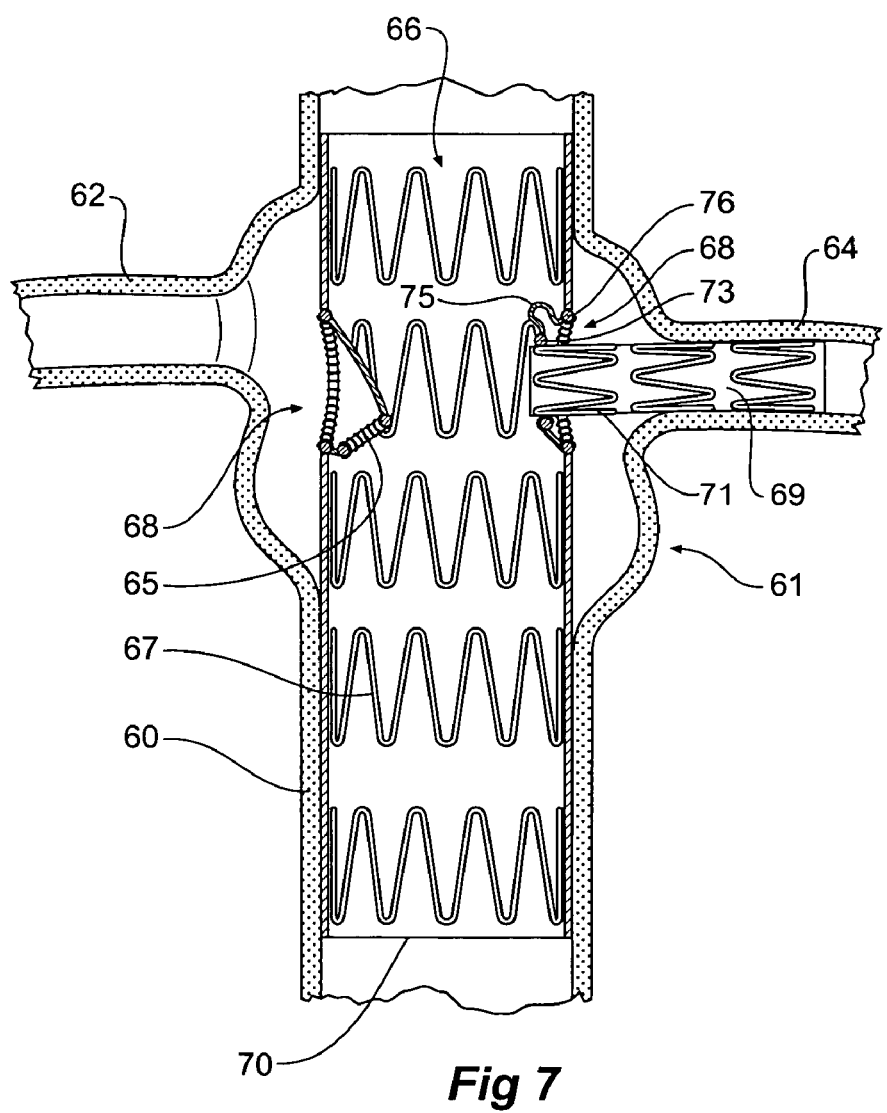
FIG. 7 shows a portion of the human aorta with a stent graft according to the present invention deployed therein.

FIG. 7 shows a schematic aorta 60 which has an aneurysm generally shown as 61 in it. The aneurysm or expanded portion of the aorta in this case includes the entrances to the renal arteries 62 and 64 within the aneurysmal region. A stent graft generally shown as 66 has been deployed to bridge or span the aneurism 61. It will be noted that in the stent graft 66 there are two fenestration assemblies 68 of the type shown in FIGS. 4 and 5 and these have been positioned so that their apertures approximate the positions of the renal arteries 62 and 64. The stent graft 66 includes a number of self expanding zig zag or Z stents 67 of the well-known Gianturco type.

In the left hand side of FIG. 7 the stent graft is shown in an as deployed condition before a side branch stent graft has been deployed and on the right hand side of the drawing in FIG. 7, a side branch stent graft has been deployed through the fenestration.

As can be seen on the left hand side of the drawing, the fenestration assembly has its inner ring 65 and hence its opening facing slightly towards the distal end 70 of the stent graft so that when a physician is attempting to deploy a guide wire from the aorta into the side branch through the stent graft 66 it will be somewhat easier to guide the guide wire through the aperture in the fenestration assembly 68.

It will be noted that, on the right hand side of the drawing, after the side branch stent graft 69 has been deployed, the inner ring 73 of the fenestration assembly 68 is engaged around the outside of the side branch stent graft 69 and the inner ring 73 has hinged to a more vertical position which means that the graft material 75 joining the inner ring 73 and the outer ring 76 of the fenestration assembly 68 is now not taut but in this condition still provides a leak proof seal for the fenestration.

The resilient inner ring provides a good sealing and retention surface for the proximal end of the side branch stent graft 69. The side branch stent graft 69 may have stents of a balloon expandable or of a self expanding type.

Figure 8:
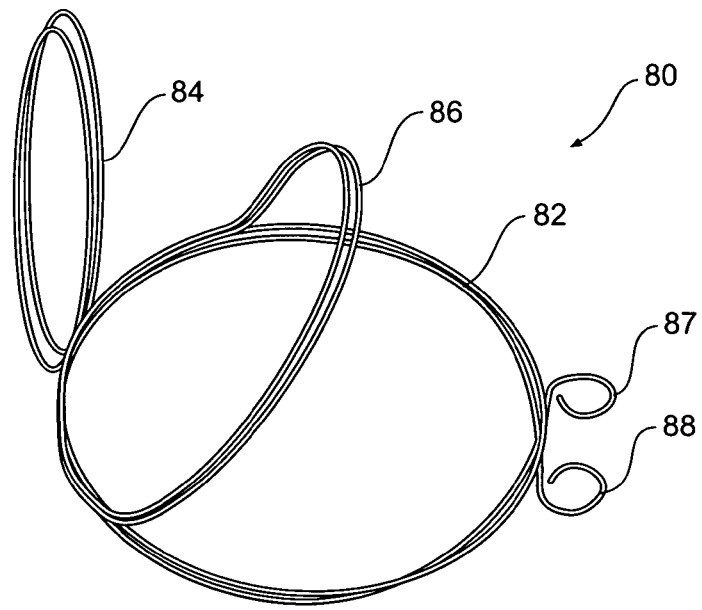
FIG. 8 shows a multiple ring arrangement suitable for a fenestration assembly according to an alternative embodiment of the invention.

FIG. 8 shows a multiple ring arrangement suitable for a fenestration assembly according to an alternative embodiment of the invention. This embodiment shows an alternative embodiment by which a ring system may be used to provide a hinge arrangement between an outer ring and an inner ring and at the same time provide an intermediate ring to give support to a graft material tube associated with the fenestration. The ring system 80 includes an outer ring system 82, an inner ring system 84 and an intermediate ring system 86. In this embodiment each of the outer ring system 82 and inner ring system 84 and the intermediate ring system 86 are formed from a continuous length of nitinol or other resilient wire with each having at least two turns of the wire. Each of the termination loops 87 and 88 of the single length of wire are provided so that there is not any "sharp" end of the wire which may tend to puncture the graft material or the vasculature. The use of nitinol or other resilient wire enables the device to be compressed when it is constrained in a deployment device for deployment.

Figure 9:
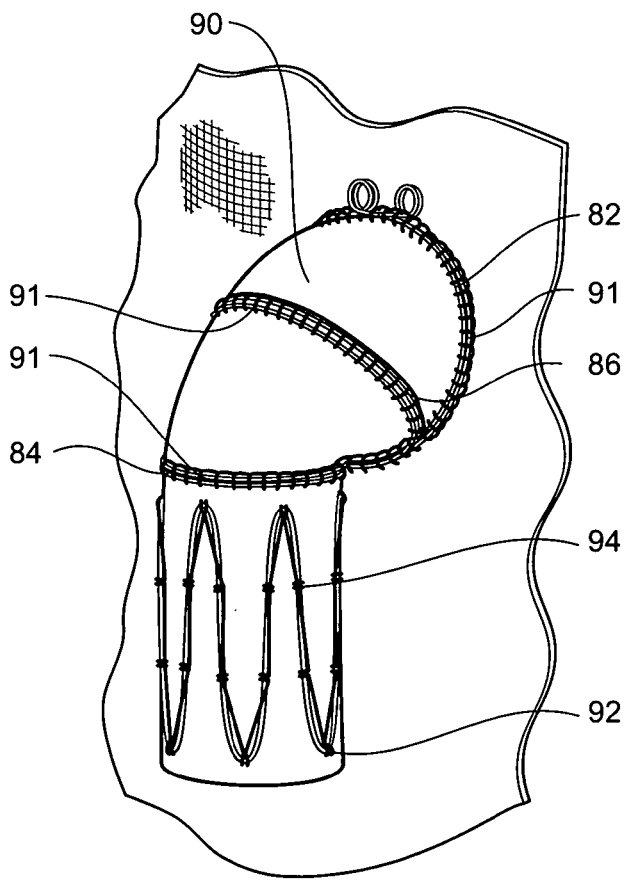
FIG. 9 shows the multiple ring arrangement of FIG. 8 with graft material stitched onto it.

FIG. 9 shows the multiple ring arrangement of FIG. 8 with a tube of graft material stitched onto it. The graft material tube 90 passes through and is stitched by stitches 91 to each of the rings 84 and 86 and one end is stitched around the ring 82 and the other end of the tube of graft material extends beyond the inner ring 84 in the form of an extension tube 92. The extension tube 92 has a self expanding zig-zag Z stent 94 of the Gianturco type fastened to it. The use of the intermediate ring gives additional clearance for the graft material tube of the side arm extension tube 92 from the main stent graft. This should assist a physician when attempting to deploy a guide wire into a renal or other artery from the main stent graft through the fenestration assembly.

Figure 10:
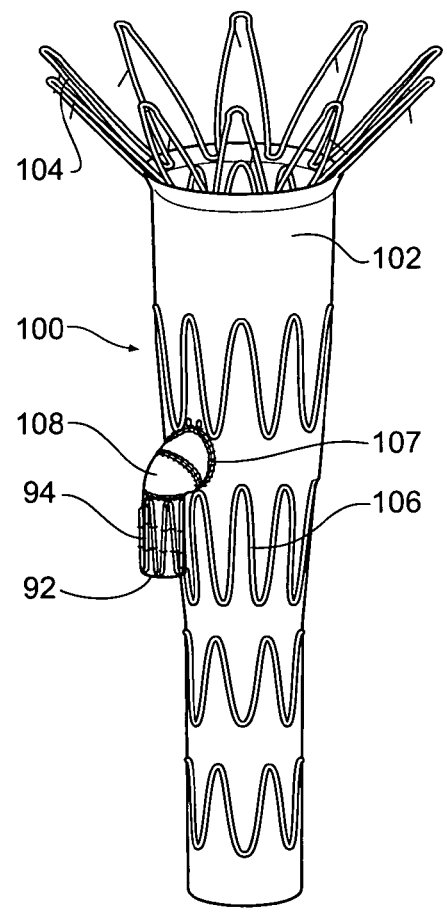
FIG. 10 shows a stent graft with a fenestration assembly according to FIGS. 8 and 9 mounted into it.

FIG. 10 shows a stent graft with a fenestration assembly according to FIGS. 8 and 9 mounted into it. The stent graft 100 has a tubular graft material body 102 with a proximally extending exposed stent 104 and a plurality of self expanding stents 106 intermediate the ends. A fenestration assembly 108 is mounted to an aperture 107 in the tubular graft material body 102 such that the extension tube 92 with its self expanding zig-zag Z stent 94 of the Gianturco type fastened to it extends distally from the aperture.

Figure 11:
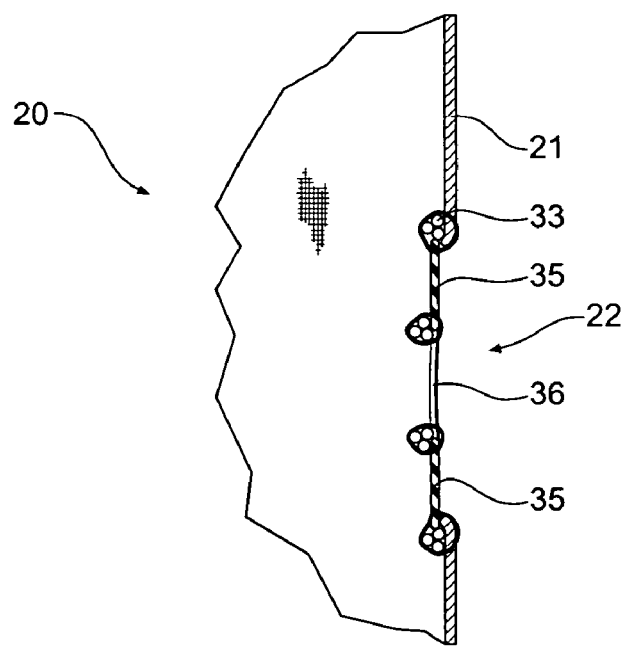
FIG. 11 shows a detailed view of an alternative embodiment of fenestration assembly according to the present invention.

FIG. 11 shows a detailed view of an alternative embodiment of fenestration assembly according to the present invention. In this embodiment the same reference numerals will be used as in FIGS. 4 and 5 for corresponding items. The wall 21 of a stent graft 20 has a fenestration assembly 22 mounted therein. The fenestration assembly 22 comprises an outer ring 33 and an inner ring 34. Each of the inner and outer rings is formed from two or three turns of a nitinol or resilient material wire. Joining the inner and outer rings is a portion of biocompatible elastic graft material 35 such as expanded polytetrafluoroethylene (ePTFE) or commercially available THORALON™ material. The biocompatible elastic or flexible graft material 35 enables the inner ring 35 to move transversely with respect to the outer ring 33 to facilitate alignment of the fenestration aperture 36 with a branch vessel into which the stent graft is deployed.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft including a wall and at least one fenestration assembly in the wall, the fenestration assembly including a first metal wire ring defining a first aperture in the wall of the stent graft and a second metal wire ring defining a smaller aperture within the first metal wire ring and a biocompatible flexible graft material extending between the first metal wire ring and the second metal wire ring, whereby to allow flexible positioning of the second metal wire ring with respect to the first metal wire ring, a third metal wire ring intermediate the first metal wire ring and the second metal wire ring, the first metal wire ring, the second metal wire ring and the third metal wire ring being joined together by an integral hinge arrangement, the first metal wire ring, the second metal wire ring, the third metal wire ring and the integral hinge arrangement comprising a single continuous length of nitinol wire or stainless steel wire, and the graft material extending between the first metal wire ring and the second metal wire ring providing a skewed frusto-conical extension between the first metal wire ring and the second metal wire ring, whereby the smaller aperture is directed towards a selected end of the stent graft.

2. A stent graft as in claim 1 further including at least one radiopaque marker at least around or concentric with each fenestration.

3. A stent graft as in claim 2 wherein the radiopaque marker comprises a biocompatible heavy metal.

4. A stent graft as in claim 1 wherein the second metal wire ring is off-center within the first metal wire ring.

5. A stent graft as in claim 1 wherein the first metal wire ring and the second metal wire ring are substantially at right angles to each other and the third metal wire ring is between the first metal wire ring and the second metal wire ring at an angle of about 45° to each of the first metal wire ring and the second metal wire ring.

6. A stent graft as in claim 1 wherein the wall of the stent graft is formed from at least one material selected from a group consisting of a biocompatible synthetic material, expanded polytetrafluoroethylene (ePTFE), a naturally occurring biomaterial and an extracellular collagen matrix (ECM) material.

7. A stent graft as in claim 1 wherein the graft material extending between the first metal wire ring and the second metal wire ring extends into the stent graft.

* * * * *